(12) United States Patent
Resconi

(10) Patent No.: US 6,872,863 B2
(45) Date of Patent: Mar. 29, 2005

(54) METHYLENE BRIDGED METALLOCENES AS OLEFIN-POLYMERIZATION CATALYST COMPONENTS

(75) Inventor: Luigi Resconi, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/737,097

(22) Filed: Dec. 16, 2003

(65) Prior Publication Data

US 2004/0147695 A1 Jul. 29, 2004

Related U.S. Application Data

(62) Division of application No. 09/831,960, filed as application No. PCT/EP99/08646 on Nov. 10, 1999, now Pat. No. 6,693,156.

(30) Foreign Application Priority Data

Nov. 18, 1998 (EP) .............................................. 98203906

(51) Int. Cl.$^7$ ............................................. C07C 13/465
(52) U.S. Cl. ........................ 585/437; 585/435; 585/436
(58) Field of Search ................................ 585/435, 437, 585/436

(56) References Cited

U.S. PATENT DOCUMENTS

| | | | | |
|---|---|---|---|---|
| 5,071,808 A | 12/1991 | Antberg et al. | ............. | 502/107 |
| 5,145,819 A | 9/1992 | Winter et al. | ................ | 502/117 |
| 5,646,322 A | 7/1997 | van Beek et al. | ............. | 556/11 |
| 5,945,553 A | 8/1999 | Küber et al. | .................. | 556/53 |
| 6,255,508 B1 | 7/2001 | Küber et al. | .................. | 556/43 |

FOREIGN PATENT DOCUMENTS

| | | | | |
|---|---|---|---|---|
| EP | 0372414 | 6/1990 | ............ | C07F/17/00 |
| EP | 0485823 | 5/1992 | ............ | C07F/17/00 |
| EP | 0575875 | 12/1993 | ............ | C08F/4/642 |
| EP | 0722949 | 7/1996 | ............ | C07F/17/00 |
| EP | 0832866 | 4/1998 | ............. | C07C/2/86 |
| WO | 9411406 | 5/1994 | ............ | C07F/17/00 |
| WO | 9602580 | 2/1996 | ............ | C08F/4/642 |
| WO | 9843931 | 10/1998 | ............ | C07C/13/28 |
| WO | 9921899 | 5/1999 | ............ | C08F/10/02 |
| WO | 9936427 | 7/1999 | ............ | C07F/17/00 |
| WO | 0121674 | 3/2001 | ............ | C08F/10/00 |

OTHER PUBLICATIONS

C. Roberts, Friedel–Crafts and related reactions, vol. II, Part 2: 1192–1193 (1964); Interscience N.Y.

A. Gol'dovskii et al., (Maslo–Zhir. Prom–st.) 1987(8): 31; Chemical Abstracts 108: 167399.

*Primary Examiner*—Caixia Lu

(57) ABSTRACT

A new class of methylene-bridged metallocenes of formula (I), wherein M is a transition metal of group 3, 4, 5, 6, lanthanide or actinide; X is a monoanionic sigma ligand; $R^1$ can be alkyl, cycloalkyl, aryl, alkylaryl or arylalkyl radicals; $R^2$ can be halogen, alkyl, cycloalkyl, aryl, alkylaryl or arylalkyl radical; p is 0–3; m is 0–2; and n is 0–4. Furthermore, the corresponding ligands, a new process for their preparation and catalysts systems containing said methylene-bridged metallocenes are described.

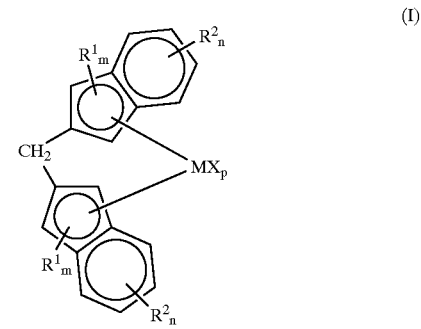

6 Claims, No Drawings

METHYLENE BRIDGED METALLOCENES AS OLEFIN-POLYMERIZATION CATALYST COMPONENTS

CROSS-REFERENCE TO RELATED APPLICATIONS

This application is a divisional of application Ser. No. 09/831,960, filed on May 16, 2001 now U.S. Pat. No. 6,693,156, which is a national phase filing under 35 U.S.C. §371 of International Application No. PCT/EP99/08646 filed Nov. 10, 1999, which claims priority to EP Application No. 98203906.7 filed Nov. 18, 1998. The entire contents of application Ser. No. 09/831,960, International Application No. PCT/EP99/08646 and EP Application No. 98203906.7, each as filed, are incorporated herein by reference.

The present invention relates to new methylene-bridged metallocenes, to the corresponding ligands, to a new process for their preparation and to the use of said metallocenes as catalytic components in the polymerization of olefins.

PRIOR ART DISCLOSURE

Stereorigid chiral metallocene compounds possessing two bridged cyclopentadienyl groups condensed to a $C_5$–$C_7$ ring are well known in the state of the art and are mainly used as catalytic components in olefin polymerization processes; in particular, metallocene compounds possessing two bridged indenyl groups are widely used in the preparation of stereoregular polyolefins.

The numbering of the substituents on the indenyl group, to which reference is made in the present application, in accordance with the IUPAC nomenclature, is the following:

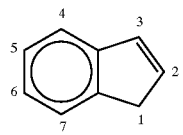

In the bridged indenyl metallocene compounds known in the state of the art, the indenyl groups are linked together by divalent radicals containing one or more carbon atoms and/or heteroatoms; the divalent bridging groups are generally linked to the 1 position of said indenyl groups, and therefore, the common indenyl metallocenes are 1-indenyl compounds. For example, the European patent application EP 0 485 823 describes a class of bridged bis(1-indenyl) metallocenes, wherein the indenyl groups have a substituent other than hydrogen in the 2 position and are bridged in the 1 position by means of a bridge containing 1 or more carbon atoms (e.g. an ethylene or isopropylidene group) or containing heteroatoms (e.g. a dimethyl-silyl or a diphenyl-silyl group).

The European patent application EP 0 372 414 describes a very broad class of bridged or unbridged metallocenes; among the many metallocenes exemplified, two specific bis-indenyl metallocene compounds are reported, wherein the ethylene group bridging the indenyl groups is linked to the 1 position of one indenyl group and to the 2 position of the other indenyl group (formulae II-1 and II-2, on page 5 of said application).

The International patent application WO 94/11406 describes a very broad class of metallocene compounds of formula R'Ind-M—(Cp)$Q_k$, wherein: Ind is an indenyl group; R' is a substituent, other than hydrogen, linked in the 2 position of said indenyl group; Cp is a cyclopentadienyl group; M is a transition metal belonging to group 3, 4, 5 or 6 of the Periodic Table of Elements; and Q is a sigma-ligand of the metal M, k being an integer linked to the valence of M. Among the huge plethora of embodiments envisaged in the reported general formula, R' can form a bridge between the 2 position of the Ind group and the Cp group of the above formula; therefore, the class of bridged bis(2-indenyl) compounds is generically described. The definition of the bridging group R' is very broad too, the preferred bridges linking the two indenyl residues being hydrocarbon groups (preferably alkenyl or arylalkenyl groups) or groups containing at least one heteroatom belonging to Group 14, 15 or 16 of the Periodic Table of the Elements. In particular, working example XIV of this application describes the synthesis of methylene-bis(2-indenyl)zirconium dichloride, comprising numerous and laborious process steps. Said bis-indenyl zirconocenes have been tested in ethylene (co) polymerization (Examples XV–XIX) and give ethylene homopolymers in very low yield and ethylene/propylene copolymers having very low molecular weights and in low yields too. Furthermore, the same Applicant has demonstrated that methylene-bis(2-indenyl)zirconium dichloride is totally inactive in propylene polymerization, as will be described in the following. The European patent application EP 0 722 949 describes a process for preparing bis-cyclopentadienyl compounds bridged by a divalent $CR^IR^{II}$ group, wherein $R^I$ is hydrogen or an alkyl radical, and $R^{II}$ is an alkyl or aryl radical. This process comprises the reaction of a ketone or an aldehyde of formula $R^IR^{II}CO$, having the desired $R^I$ and $R^{II}$ groups, with a cyclopentadienyl compound, in the presence of a base and of an oxygen-containing solvent having an atomic ratio carbon/oxygen not higher than 3. However, the class of bis-cyclopentadienyl compounds obtainable with this process does not encompass compounds bridged with a methylene group; moreover, when $R^IR^{II}CO$ is reacted with an indenyl compound in the presence of a base, according to the above-mentioned process conditions, only bridged bis(1-indenyl) derivatives are obtained.

The European patent application EP 0 832 866 describes a process for preparing methylene-bridged bis-cyclopentadienyl compounds by reacting, in a two- or more-phases system, one or two cyclopentadienyl compounds with formaldehyde in the presence of a base and of a phase-transfer catalyst. Nevertheless, this application does not disclose any compounds wherein the two indenyl groups are linked in position 2; in fact, as evident from working example 1, this process leads to bis-(1-indenyl) derivatives and does not allow bridged bis(2-indenyl) compounds to be obtained.

WO 98/43931 (app. no. PCT/EP 98/01930), in the name of the same Applicant, describes a process for preparing methylene-bridged bis-cyclopentadienyl compounds, comprising the reaction of formaldehyde with a suitable cyclopentadienyl compound, in the presence of a base and a solvent having a dielectric constant, measured at 25° C., higher than 7. Also in this case, the process allows only bis-indenyl compounds to be obtained, wherein the two indenyl moieties are bridged in position 1.

The Prins reaction (i.e., the acid-catalyzed condensation of carbonyl compounds and olefins) on indene has been described several times in the state of the art; as reported by Carleton W. Roberts (*Friedel-Crafts and related reactions*, vol., Part 2, page. 1192–1193, 1964, Interscience N.Y.), the reaction of indene with formaldehyde in the presence of acids does not give bis-indenyl products, but leads to the dioxane 1-hydroxy-2-hydroxymethylindan methylene ether as the major product. The same reaction was carried out by A. E. Gol'dovskii et al. (Maslo-Zhir. Prom-st., 1987(8): 31; Chemical Abstracts 108:167399), who obtained said dioxane from indene and $CH_2O$, in the presence of $H_2SO_4$.

From what reported above, it would be highly desirable to provide methylene-bridged bis(2-indenyl) derivatives, obtainable by means of an easy and advantageous route for the preparation thereof.

SUMMARY OF THE INVENTION

The Applicant has now unexpectedly found a new class of metallocenes, particularly active as catalyst components for the polymerization of olefins; said metallocenes are characterized by the presence of two indenyl groups bridged in the 2 position by means of a methylene group.

Therefore, an object of the present invention is a methylene-bridged metallocene of formula (I):

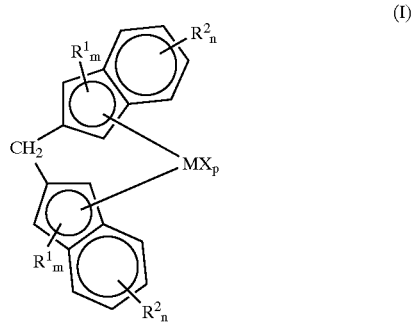

(I)

wherein:

M is a transition metal belonging to group 3, 4, 5, 6 or to the lanthanide or actinide groups of the Periodic Table of the Elements (new IUPAC notation);

the substituents X, the same or different from each other, are monoanionic sigma ligands selected from the group consisting of hydrogen, halogen, —R, —OR, —OSO$_2$CF$_3$, —OCOR, —SR, —NR$_2$ and —PR$_2$ groups, wherein the R substituents are linear or branched, C$_1$–C$_{20}$ aliphatic hydrocarbon, C$_3$–C$_{20}$ cycloalkyl, C$_6$–C$_{20}$ aryl, C$_7$–C$_{20}$ alkylaryl or C$_7$–C$_{20}$ arylalkyl radicals, optionally containing one or more atoms belonging to groups 13–17 of the Periodic Table of the Elements (new IUPAC notation), such as B, N, P, Al, Si, Ge, O, S and F atoms, and two R substituents may form a 5–7-membered ring; preferably, the substituents X are the same;

the substituents R$^1$ and R$^2$, the same or different from each other, are selected from the group consisting of linear or branched, C$_1$–C$_{20}$ aliphatic hydrocarbon, C$_3$–C$_{20}$ cycloalkyl, C$_6$–C$_{20}$ aryl, C$_7$–C$_{20}$ alkylaryl and C$_7$–C$_{20}$ arylalkyl radicals, optionally containing one or more atoms belonging to groups 13–17 of the Periodic Table of the Elements (new IUPAC notation; such as B, N, P, Al, Si, Ge, O, S and F atoms), —OR, —SR, —NR$_2$, N-pyrrolyl, N-indolyl, —PR$_2$, —BR$_2$ and —SiR$_3$ groups, wherein the R substituents have the meaning reported above, or two adjacent R$^2$ substituents form a ring having from 4 to 8 carbon atoms;

p is an integer ranging from 0 to 3, being equal to the oxidation state of the metal M minus 2;

m is an integer ranging from 0 to 2; n is an integer ranging from 0 to 4;

with the proviso that, when m is 0, then n is different from 0.

Another object of the present invention is a catalyst for the polymerization of olefins comprising the product obtainable by contacting:

(A) one or more methylene-bridged metallocenes of formula (I), as described above; and (B) a suitable activating cocatalyst.

Furthermore, the present invention provides a process for the polymerization of olefins comprising the polymerization reaction of one or more olefinic monomers in the presence of a catalyst as described above.

It is another object of the present invention a ligand of formula (II):

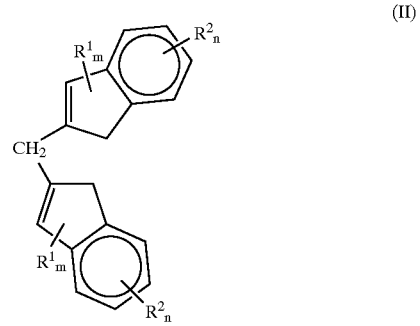

(II)

wherein R$^1$, R$^2$, m and n have the meaning reported above.

The present invention further concerns a new and inventive process for the preparation of the above ligands of formula (II), comprising reacting formaldehyde or a derivative thereof with a indene of formula (III):

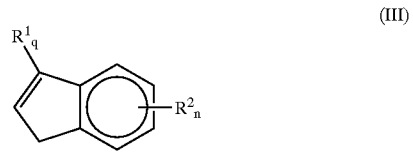

(III)

wherein R$^1$, R$^2$ and n have the meaning reported above, and q is 0 or 1, in the presence of a Brønsted acid, wherein the molar ratio between said compound (III) and formaldehyde is $\geq 1$. When in the ligand of formula (II) m is $\neq 0$, then the substituents R$^1$ may also be introduced on the cyclopentadienyl ring by reacting a corresponding ligand of formula (II) having m=0 with a suitable amount of a deprotonating agent R$^3$MgBr, R$^3$MgCl or R$^3{}_j$B, wherein R$^3$ may have the same meaning of R$^1$; B is an alkaline or alkaline-earth metal, and j is 1 or 2, and then with a suitable amount of an alkylating agent R$^1$X', wherein R$^1$ have the meaning reported above and X' is halogen.

DETAILED DESCRIPTION OF THE INVENTION

The methylene-bridged metallocenes of formula (I), the catalysts for the polymerization of olefins containing them, the ligands of formula (II) and the process for their preparation, according to the present invention, will be better described in the following detailed description.

It is an object of the present invention a methylene-bridged metallocene of formula (I), as reported above, wherein the metal M preferably belongs to group 4 of the Periodic Table of the Elements, and more preferably is Zr or Hf.

The X substituents are preferably Cl, Br or methyl, and are preferably the same.

R$^1$ is preferably selected from the group consisting of methyl, ethyl. n-propyl, i-propyl, n-butyl, t-butyl, phenyl, benzyl, trimethyl-silyl and diphenylphosphino. The choice of the preferred R$^1$ depends also on the nature of the final polymer, as will be evident from what reported below.

R$^2$ is preferably selected form the group consisting of halogen, methyl, ethyl, n-propyl, i-propyl, n-butyl, t-butyl, phenyl and benzyl.

The variable m is an integer ranging from 0 to 2; the variable n is an integer ranging from 0 to 4.

Non-limiting examples of methylene-bridged metallocenes corresponding to formula (I), according to the present invention, are:

rac- and meso-methylene-bis(1-methyl-2-indenyl)zirconium dichloride and dimethyl, methylene-bis(1,3-dimethyl-2-indenyl)zirconium dichloride and dimethyl, methylene-bis(4,7-dimethyl-2-indenyl)zirconium dichloride and dimethyl, rac- and meso-methylene-bis(1-ethyl-2-indenyl)zirconium dichloride and dimethyl, rac-methylene-bis(1-t-butyl-2-indenyl)zirconium dichloride and dimethyl, rac-methylene-bis(1-t-butyl-2-indenyl)hafnium dichloride and dimethyl, rac- and meso-methylene-bis(5-t-butyl-2-indenyl)zirconium dichloride and dimethyl, rac- and meso-methylene-bis(1-trimethylsilyl-2-indenyl)zirconium dichloride and dimethyl, rac- and meso-methylene-bis(1-trimethylsilyl-3-methyl-2-indenyl)zirconium dichloride and dimethyl, rac-methylene-bis(1-phenyl-2-indenyl)zirconium dichloride and dimethyl, rac-methylene-bis(1-benzyl-2-indenyl)zirconium dichloride and dimethyl, rac- and meso-methylene-bis(4-phenyl-2-indenyl)zirconium dichloride and dimethyl, rac-methylene-bis(1-PPh$_2$-2-indenyl)zirconium dichloride and dimethyl, rac-methylene-bis(1-B(cyclohexyl)$_2$-2-indenyl)zirconium dichloride and dimethyl, and rac- and meso-methylene-bis(4-t-butyl-7-methyl-2-indenyl)zirconium dichloride and dimethyl.

The methylene-bridged metallocenes of formula (I) can be prepared by reaction of the corresponding ligands of formula (II) first with a compound capable of forming a delocalized anion on the cyclopentadienyl ring, and then with a compound of formula $MX_{p+2}$, wherein M, X and p are defined as above, according to common procedures known in the state of the art. When, in the metallocene of formula (I), one or more X groups are other than halogen, it is necessary to substitute one or more halogens Z of the metallocene halide, obtained as reported above, with one or more substituents X other than halogen. The substitution reaction can be carried out by standard procedures, for example, when the substituents X are alkyl groups, by reacting the metallocene halide with alkylmagnesium halides (Grignard reagents) or with alkyllithium compounds.

According to another embodiment, when in formula (I) the X groups have the meaning of —R, as defined above, the methylene-bridged metallocenes of the invention can be obtained by reacting directly a ligand of formula (II) with at least one molar equivalent of a compound of formula $MX_s$, in the presence of at least (p+2) molar equivalents of a suitable alkylating agent, wherein R, M and X have the meaning reported above and s is an integer corresponding to the oxidation state of the metal M and ranges from 3 to 6. Said alkylating agent can be an alkaline or alkaline-earth metal, such as LiR or MgR$_2$, or a Grignard reagent, such as RMgCl or RMgBr, as described in WO 99/36427 (priority European app. no. 98200077.0), in the name of the same Applicant.

It is another object of the invention a ligand having the above-mentioned formula (II), wherein R$^1$, R$^2$, m and n have the meaning reported above. According to the present invention, the ligands of formula (II) are prepared by means of a new process, particularly simple and efficient, using cheap starting materials and comprising a single reaction step with very high yields. Furthermore, said process does not require laborious and time-consuming purification procedures, being particularly suitable to large-scale production.

The process of the invention comprises reacting formaldehyde or a derivative thereof with an indene of formula (III), as reported above, in the presence of a Brønsted acid, wherein the molar ratio between the compound (III) and formaldehyde is $\geq 1$.

Said process is preferably carried out in an aprotic solvent, which may be polar or apolar; a preferred polar solvent is toluene, while a preferred apolar solvent is n-decane.

Said Brønsted acid is preferably selected from the group consisting of p-toluensulphonic acid, acetic acid, methanesulphonic acid, HCl, H$_2$SO$_4$, HBF$_4$ and mixtures thereof. Formaldehyde is preferably used in the form of a solution in water (formalin) or in the polymeric form (paraformaldehyde). However, other forms of formaldehyde as well as its solutions at different concentrations can be suitably used. Suitable derivatives of formaldehyde to be used in the process of the invention are compounds able to release formaldehyde under reaction conditions; preferred derivatives of formaldehyde are 1,3-dioxolane and trioxane. According to the process of the invention, formaldehyde or a derivative thereof can be reacted with an indene of formula (III) at any temperature above the melting point of the solvent. The temperature is preferably lower than the boiling point of the solvent, and more preferably is comprised between about 50° C. and 100° C.

The reaction time is not limiting, depending to a large extent on the acid, solvent and substrate used, on the concentration of the reactants and on the temperature of the reaction.

The molar ratio between said indene of formula (III) and formaldehyde or a derivative thereof can vary over a wide range; said molar ratio is $\geq 1$, and preferably is about 2.

The molar ratio between said acid and said indene of formula (III) can vary over a wide range; the molar ratio acid/indene (III) preferably ranges from 0.01 to 2, and more preferably from 0.1 to 1.5. The methylene-bridged ligands (II) obtained from the process of the present invention can be isolated according to standard procedures known in the state of the art, e.g. by recrystallization from a suitable solvent.

When in the ligand of formula (III) m is $\neq 0$, the substituents R$^1$ can also be introduced on the cyclopentadienyl ring by reacting the corresponding ligand of formula (II) wherein m=0 with a suitable amount of a deprotonating agent R$^3$MgBr, R$^3$MgCl or R$^3_j$B, wherein R$^3$ may have the same meaning of R$^1$, B is an alkaline or alkaline-earth metal, and j is 1 or 2, and then with a suitable amount of an alkylating agent R$^1$X', wherein R$^1$ and X' have the meaning reported above.

Preferably, the compound of formula (II) wherein m=0 is reacted with at least 2 equivalents of said deprotonating agent, at a temperature ranging from −78° C. to 20° C., for a time of 1–24 hours. The reaction is preferably conducted in an organic solvent selected from the group consisting of THF, Et$_2$O, toluene and mixtures thereof. Said deprotonating agent is preferably selected from the group consisting of RLi and KH.

The process of the present invention has the advantage of allowing the synthesis of the new ligands (II) in a rapid and easy one-step reaction; these ligands could not be obtained or could be only hardly obtained, in very low yields and with laborious and time consuming procedures, according to the processes known in the state of the art.

The methylene-bridged metallocenes according to the present invention can be advantageously used as catalytic components for the polymerization of olefins. Thus, another object of the present invention is a catalyst system for the polymerization of olefins, comprising the product obtainable by contacting:
(A) one or more bridged metallocene compounds of formula (I), as described above, and
(B) a suitable activating cocatalyst.

Activating cocatalysts suitable as component (B) in the catalysts of the invention are linear, branched or cyclic alumoxanes, containing at least one group of the type:

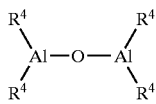

wherein the substituents $R^4$, the same or different from each other, are a linear or branched, $C_1$–$C_{20}$ aliphatic hydrocarbon, $C_3$–$C_{20}$ cycloalkyl, $C_6$–$C_{20}$ aryl, $C_7$–$C_{20}$ alkylaryl, $C_7$–$C_{20}$ arylalkyl radicals, optionally containing Si and Ge atoms, or $R^4$ is a group —O—Al($R^4$)$_2$. $R^4$ is preferably methyl, ethyl, isobutyl or 2,4,4-trimethyl-pentyl.

Examples of alumoxanes suitable as activating cocatalysts in the catalysts according to the present invention are methylalumoxane (MAO), tetra-isobutyl-alumoxane (TIBAO), tetra-2,4,4-trimethylpentylalumoxane (TIOAO) and tetra-2-methyl-pentylalumoxane. Mixtures of different alumoxanes can also be used.

Activating cocatalysts suitable as component (B) in the catalysts of the invention are also the products of the reaction between water and an organometallic aluminum compound, preferably of formula $AlR^5_3$ or $Al_2R^5_6$, wherein $R^5$ has the meaning reported above. Particularly suitable are the organometallic aluminum compounds of formula (II) described in EP 0 575 875 and those of formula (II) described in WO 96/02580. Moreover, suitable cocatalysts are the ones described in WO 99/21899 (priority European app. no. 97203332.8) and in the European app. no. 99203110.4. Non-limiting examples of organometallic aluminum compounds of formula $AlR^4_3$ or $Al_2R^4_6$ are:
tris(methyl)aluminum, tris(isobutyl)aluminum,
tris(isooctyl)aluminum, bis(isobutyl)aluminum hydride,
methyl-bis(isobutyl)aluminum, dimethyl(isobutyl) aluminum,
tris(isohexyl)aluminum, tris(benzyl)aluminum,
tris(tolyl)aluminum, tris(2,4,4-trimethylpentyl)aluminum,
bis(2,4,4-trimethylpentyl)aluminum hydride, isobutyl-bis(2-phenyl-propyl)aluminum,
diisobutyl-(2-phenyl-propyl)aluminum, isobutyl-bis(2,4,4-trimethyl-pentyl)aluminum,
diisobutyl-(2,4,4-trimethyl-pentyl)aluminum, tris(2,3-dimethyl-hexyl)aluminum,
tris(2,3,3-trimethyl-butyl)aluminum, tris(2,3-dimethyl-butyl)aluminum,
tris(2,3-dimethyl-pentyl)aluminum, tris(2-methyl-3-ethyl-pentyl)aluminum,
tris(2-ethyl-3-methyl-butyl)aluminum, tris(2-ethyl-3-methyl-pentyl)aluminum,
tris(2-isopropyl-3-methyl-butyl)aluminum and tris(2,4-dimethyl-heptyl)aluminum.

Particularly preferred aluminum compounds are trimethylaluminum (TMA), tris(2,4,4-trimethylpentyl)aluminum (TIOA), triisobutylaluminum (TIBA), tris(2,3,3-trimethyl-butyl)aluminum and tris(2,3-dimethyl-butyl)aluminum.

Mixtures of different organometallic aluminum compounds and/or alumoxanes can also be used.

The molar ratio between aluminum and the metal M of the methylene-bridged metallocene is preferably comprised between about 10:1 and about 50,000:1, and preferably between about 100:1 and about 4,000:1.

In the catalyst system according to the present invention, both said methylene-bridged metallocene and said alumoxane can be pre-reacted with an organometallic aluminum compound of formula $AlR^4_3$ or $Al_2R^4_6$, wherein the $R^4$ substituents have the meaning reported above.

Further activating cocatalysts suitable as component (B) in the catalysts of the invention are those compounds capable of forming an alkylmetallocene cation; preferably, said compounds have formula $Y^+Z^-$, wherein $Y^+$ is a Broensted acid capable of donating a proton and of reacting irreversibly with a substituent X of the compound of formula (I), and $Z^-$ is a compatible non-coordinating anion, capable of stabilizing the active catalytic species which result from the reaction of the two compounds, and which is sufficiently labile to be displaceable by an olefinic substrate. Preferably, the $Z^-$ anion comprises one or more boron atoms. More preferably, the anion $Z^-$ is an anion of formula $BAr_4^{(-)}$, wherein the Ar substituents, the same or different from each other, are aryl radicals such as phenyl, pentafluorophenyl, bis(trifluoro-methyl)phenyl. Tetrakis-pentafluorophenyl-borate is particularly preferred. Moreover, compounds of formula $BAr_3$ can be conveniently used.

The catalysts of the present invention can also be used on inert supports. This is achieved by depositing the methylene-bridged metallocene (A), or the product of its reaction with the activating cocatalyst (B), or the component (B) and then the metallocene (A), on a suitable inert support, such as silica, alumina, magnesium halides, olefin polymers or prepolymers, such as polyethylenes, polypropylenes or styrene-divinylbenzene copolymers.

The thus obtained supported catalyst system, optionally in the presence of alkylaluminum compounds, either untreated or pre-reacted with water, can be usefully employed in gas-phase polymerization processes.

The present invention also provides a process for the homo or copolymerization of olefins, comprising the polymerization reaction of one or more olefinic monomers in the presence of a catalyst system as described above. Representative examples of olefinic monomers which may be used in the polymerization process of the invention are ethylene, alpha-olefins such as propylene, 1-butene, 1-hexene, 4-methyl-1-pentene and 1-octene, and non-conjugated diolefins such as 1,5-hexadiene.

The catalyst systems of the invention are particularly advantageous in ethylene and propylene homopolymerizations, where they exert higher activities when compared to prior art analogues. Moreover, by changing the substitution patterns of the methylene-bridged metallocenes of the invention, it is possible to obtain in high yields, at temperatures of industrial interest, polyethylenes and polypropylenes having intrinsic viscosity (I.V.) ranging from very low values (oils or waxes) to high values (I.V.>1 dl/g). Therefore, an advantage of the metallocenes of the invention is that they allow polymers having a wide range of molecular weights to be obtained.

From propylene homopolymerization, by using the metallocenes of formula (I) wherein M is Zr, according to the invention, it is possible to obtain atactic propylene oligomers, terminated with vinylidene end-groups, which are particularly useful as lubricants, functionalizable monomers and chemical intermediates. By using the metallocenes of formula (I) wherein M is Hf, atactic polypropylene having higher molecular weight values are obtainable.

From ethylene homopolymerization, it is possible to obtain linear α-olefins having a Pn (Number Average Degree of Polymerization) ranging from 50 to 500, and preferably from 80 to 350; these α-olefins have more than 90% of terminal vinyl unsaturations (on the total number of terminal vinyl and vinylidene unsaturations). By varying the substitution pattern on the catalysts according to the invention, and in particular by using methylene-bridged bis(1-methyl-2- indenyl)metallocenes, it is possible to obtain linear α-olefins having a percentage of terminal vinyl unsaturations higher than 90%, preferably higher than 95%, thus providing useful α-olefinic PE waxes. Moreover said α-olefins are linear, having a number of total branches preferably lower than 1/100 carbon atoms, and more preferably lower than 0.1/100 C. These α-olefins are particularly useful as polymerization monomers and chemical intermediates.

When the present catalyst systems are used in the copolymerization of ethylene and propylene, the methylene-bridged metallocenes of the invention allow to obtain copolymers in high yields, having a broad range of comonomer content.

The polymerization process can be carried out in the liquid phase, optionally in the presence of inert hydrocarbon solvents, or in the gas phase. The hydrocarbon solvent can be either aromatic, such as toluene, or aliphatic, such as propane, hexane, heptane, isobutane and cyclohexane.

The polymerization temperature is generally comprised between −100° C. and +150° C., and more particularly between 50° C. and 100° C. The lower is the polymerization temperature, the higher are the molecular weights of the polymers obtained.

The molecular weight of the polymers can be further varied by changing the type or the concentration of the catalytic components or by using molecular weight regulators, for example hydrogen.

The molecular weight distribution can be varied by using mixtures of different metallocenes, or by carrying out the polymerization in several steps, that differ with respect to the temperatures of polymerization and/or the concentrations of molecular weight regulators.

An advantageous embodiment of the process for the polymerization of olefins, according to the present invention, is the use of a metallocene of formula (I) in combination with other metallocenes known in the state of the art, so to obtain polyethylenes with a well-defined bimodal distribution. More specifically, a metallocene of formula (I) able to produce PE waxes having low molecular weight, such as methylene-bridged bis(1-methyl-2-indenyl) metallocenes, may be used in mixture with one or more metallocenes known in the state of the art, able to yield polyethylenes having high molecular weights; by combining the above metallocenes, it is possible to obtain bimodal or multimodal polyethylenes which, despite the presence of the PE wax fraction of the invention (having very low molecular weight), do not have significant amounts of extractables.

The polymerization yields depend on the purity of the metallocene compound of the catalyst. The metallocene compounds obtained by the process of the invention can be used as they are, or they can undergo purification treatments.

The components of the catalyst can be brought into contact with each other prior to polymerization. The duration of contact is generally between 1 and 60 minutes, preferably between 5 and 20 minutes. The pre-contact concentrations for the metallocene component (A) are between 1 and $10^{-8}$ mole/l, whereas for component (B) they are between 10 and $10^{-5}$ mole/l. Precontact is generally effected in the presence of a hydrocarbon solvent and, if suitable, in the presence of small amounts of monomer.

The following experimental examples are given for illustrative and not limiting purposes.

General Procedures and Characterizations

All operations were performed under nitrogen by using conventional Schlenk-line techniques. Solvents were purified by degassing with $N_2$ and passing over activated (8 hours, $N_2$ purge, 300 ° C.) $Al_2O_3$, and stored under nitrogen.

The metallocenes and the ligands thereof were characterized by the following methods:

$^1$H-NMR

All compounds were analyzed on an AC 200 Bruker spectrometer by $^1$H NMR ($CDCl_3$, referenced against the peak of residual $CHCl_3$ at 7.25 ppm, or $CD_2Cl_2$, referenced against the peak of residual $CHDCl_2$ at 5.35 ppm). All NMR solvents were dried over $LiAlH_4$, $P_2O_5$ or $CaH_2$ and distilled before use. Preparation of the samples was carried out under nitrogen using standard inert atmosphere techniques.

The polymers were characterized by the following methods:

$^{13}$C-NMR

The $^{13}$C-NMR analyses were performed on a Bruker DPX 400 MHz instrument, in tetrachlorodideuteroethane at 130° C.

Pn (Number Average Degree of Polymerization), evaluated by $^1$H-NMR analysis, gives a molecular weight measure for low molecular weight products, assuming one double bond per chain, as described by Resconi et al. (JACS, 120:2308–2321, 1998).

Viscosity Measurements

The intrinsic viscosity (I.V.) was measured in tetrahydronaphtalene (THN) at 135° C. The polymer molecular weights were determined from the viscosity values.

IR Analysis

IR analysis were performed on a Nicolet 20 instrument, on samples of 0.1 mm thickness.

DSC Analysis

The $T_g$ values were measured on a DSC Mettler instrument. The samples, sealed into aluminum pans, were first heated to 200° C. at 20° C./min and kept at this temperature for 5 minutes. After cooling to 0° C. at 20° C./min, the sample was left for 5 minutes at 0° C. and finally heated to 200° C. at 10° C./min. In this second heating run, the peak temperature was assumed as melting temperature (Tm) and the area as global melting enthalpy ($\Delta H_f$).

Catalyst Components

Methylalumoxane (MAO)

(1) A commercial (Witco, MW 1400) 10% w/w toluene solution of MAO (1.7M) was used as such.

(2) Alternatively, the commercial sample was dried in vacuum to a free-flowing powder (residual $AlMe_3$ about 3–5 mol %).

Tris(2,4,4-trimethyl-pentyl)aluminoxane (TIOAO)

Tris(2,4,4-trimethyl-pentyl)aluminum (TIOA) was purchased from Witco and was diluted to a 1M solution in hexane. 3.45 ml of said solution were added at room temperature to 5 ml of toluene, previously deoxygenated and distilled over triisobutylaluminum. 0.031 ml of $H_2O$ were then added at room temperature with a syringe and the resulting solution was stirred for 10 minutes at room temperature.

Catalyst Mixture

The catalyst mixture was prepared by adding the desired amount of the metallocene to the proper amount of the MAO or TIOAO solution, thus obtaining a solution which was stirred for 10 minutes at room temperature and then injected into the autoclave, at the polymerization temperature, in the presence of the monomer.

Metallocene Synthesis

Synthesis 1

Methylene-bis(2-indenyl)zirconium dichloride (a-1) Synthesis of bis(2-indenyl)methane (with para-formaldehyde)

In a 500 mL flask equipped with magnetic stirring bar were introduced 16.2 g (0.139 moles) of indene, 2.78 g (0.093 moles) of para-formaldehyde and 5.2 g (0.027 moles) of para-toluenesulphonic acid in 200 ml of toluene; the mixture was heated to 80° C. and was maintained under stirring for 1 hour at 80° C. Then the reaction was quenched with water/$NaHCO_3$; the conversion, measured by gas chromatographic analysis, was 65.8%. The organic layer was separated, washed with water and brought to dryness under reduced pressure. The crude product was crystallized upon standing at room temperature, and then was further purified by washing with pentane or MeOH, thus isolating bis(2-indenyl)methane.

$^1$H-NMR (CDCl$_3$): δ 7.38 (d, 2H), 7.28 (t, 2H), 7.25 (d, 2H), 7.12 (t, 2H), 6.6 (s, 2H, =CH), 3.65 (s, 2H, bridge CH$_2$), 3.38 (s, 4H, 2×CH$_2$).

(a-2) Synthesis of bis(2-indenyl)methane (with 1,3-dioxolane and para-toluenesulphonic acid)

2.9 g of para-toluenesulphonic acid (15 mmol), 100 mL of toluene, 5.4 mL of 1,3-dioxolane (Aldrich, MW 74.08, 77 mmol) and 10 g of indene (77 mmol) were placed in this order in a 250 mL flask equipped with magnetic stirring bar, thermometer and reflux condenser. This mixture was heated at 80° C. in 20 minutes and stirred at 80° C. for 6 hours. After cooling to room temperature, the mixture was poured onto ice/NaHCO$_3$ and the organic layer separated in a funnel. The water layer was washed with Et$_2$O (2×150 mL), the organic layers were combined, dried with NaSO$_4$, filtered and concentrated in vacuo to yield the crude target product, with a conversion of 59%.

(a-3) Synthesis of bis(2-indenyl)methane (with 1,3-dioxolane and methane-sulphonic acid)

The procedure reported in synthesis 1(a-2) was repeated by using 1.43 g of methane-sulphonic acid (14 mmol), 100 mL of toluene, 5.2 mL of 1,3-dioxolane (74 mmol) and 9.2 g of indene (71 mmol), obtaining the crude target product, with a conversion of 49.9%.

(b) Synthesis of methylene-bis(2-indenyl)zirconium dichloride 0.29 g (1.19 mmol) of bis(2-indenyl)methane, prepared as described above, were dissolved in 40 ml ether and cooled to −78° C. Then 1.6 ml of a 1.6 M solution of n-BuLi in hexane (2.1 equivalents) were added by syringe. It was allowed to warm to room temperature. After 90 minutes at room temperature it was cooled to −78° C. and 0.29 g ZrCl$_4$, suspended in 30 ml Et$_2$O, was added. On allowing to warm to room temperature and stirring for 2 hours, the color changed from brown to yellowish. The solvent was removed under vacuum and the powder washed with Et$_2$O and then hexane to give 300 mg of methylene-bis(2-indenyl)zirconium dichloride as a yellow powder.

$^1$H NMR (CD$_2$Cl$_2$): δ 7.51 (dd, 4H), 7.24 (dd, 4H), 6.1 (s, 4H, =CH), 4.28 (s, 2H, bridge CH$_2$).

Synthesis 2
Methylene-bis(4,7-dimethyl-2-indenyl)zirconium dichloride (a-1) Synthesis of bis(4,7-dimethyl-2-indenyl)methane (with para-toluensulphonic acid)

In a 500 mL flask equipped with magnetic stirring bar were introduced 10 g (0.069 moles) of 4,7-dimethyl-indene, 1.04 g (0.035 moles) of formalin and 2.64 g (0.014 moles) of para-toluenesulphonic acid in 100 ml of toluene; the mixture was heated to 80° C. and was maintained under stirring for 3 hours at 80° C. Then the reaction was quenched with water/NaHCO$_3$; the conversion, measured by gas chromatographic analysis, was 82.4%. The organic layer was separated, washed with water and brought to dryness under reduced pressure. The crude product was crystallized upon standing at room temperature, and then was further purified by washing with pentane or MeOH, thus isolating 5.1 g of bis(4,7-dimethyl-2-indenyl)methane (purity of 90.2% by G.C.; yield=44.1%).

$^1$H NMR (CDCl$_3$): 7.1–6.9 (m, 4H); 6.78 (s, 2H); 3.79 (s, 2H); 3.29 (s, 4H); 2.45 (s, 6H); 2.33 (s, 6H).

(a-2) Synthesis of bis(4,7-dimethyl-2-indenyl)methane (with H$_2$SO$_4$)

In a 250 mL flask equipped with magnetic stirring bar were introduced 5 g (34.7 mmoles) of 4,7-dimethyl-indene, 0.57 g (0.19 mmoles) of para-formaldehyde and 0.21 g (1.7 mmoles) of concentrated sulphuric acid in 50 ml of benzene; the mixture was heated at reflux for 2 hours. Then the reaction crude was dissolved in 200 ml CH$_2$Cl$_2$, washed with a saturated solution of NaHCO$_3$ and with water. After drying over anhydrous magnesium sulphate, the solution was filtered and concentrated to give bis(4,7-dimethyl-2-indenyl)methane as a slightly yellow solid (yield=62%). The product was further purified by crystallization from isopropanol. The results of the $^1$H-NMR analysis correspond to the ones reported above.

(b) Synthesis of methylene-bis(4,7-dimethyl-2-indenyl) zirconium dichloride 2.24 g of bis(4,7-dimethyl-2-indenyl)methane (purity 89% by G.C., 6.66 mmol), obtained as reported above, were dissolved in 63 mL Et$_2$O, in a Schlenk tube with magnetic stirring bar; the solution was cooled to −80° C. and 6 mL of a 2.5 M solution of BuLi in hexane (15 mmol) were added dropwise in 10 minutes. The obtained solution was allowed to warm to room temperature and stirred for 6 hours, thus obtaining a pink-red suspension, which was then cooled to −80° C. and added to a slurry of 1.6 g of ZrCl$_4$ (6.87 mmol) in 63 mL of pentane, in a 250 mL flask at −80° C. After warming to room temperature, the mixture was stirred overnight. The yellow-brown suspension was dried to a free-flowing powder. This powder was slurried in 100 mL of CH$_2$Cl$_2$, transferred into an extraction apparatus and extracted with refluxing CH$_2$Cl$_2$ for 6 hours (a yellow precipitate formed in the collecting flask during the extraction). At the end of the extraction, CH$_2$Cl$_2$ was concentrated to 20 mL, then cooled to −20° C. overnight, and finally filtered. The residue was washed with CH$_2$Cl$_2$ until the washing turned from brown to straw-yellow, and finally dried, to yield 1.215 g of yellow solid. $^1$H NMR analysis shows the presence of the pure target compound CH$_2$(4,7-Me$_2$-2-Ind)$_2$ZrCl$_2$.

$^1$H NMR (CD$_2$Cl$_2$, ref. CDHCl$_2$ at 5.377 ppm, room temp.): Ar—CH$_3$, 2.451, s; CH$_2$, 4.397, s; Cp-H, 6.058, s; Ar, 6.976, s.

An additional 0.734 g of product were recovered from the filtrate and washings combined, by drying and washing with toluene. Combined yield 63%.

Synthesis 3
Rac-Methylene-bis(1-methyl-2-indenyl)zirconium dichloride (a-1) Synthesis of bis(3-methyl-2-indenyl)methane from bis(2-indenyl)methane 5.11 g of bis(2-indenyl)methane (91.1% by G.C., 19 mmol), obtained as reported in Synthesis 1(a), were dissolved in 50 mL T.HF, in a 100 mL Schlenk tube with magnetic stirring bar, and the solution was cooled to −40° C.; 27 mL of a 1.6 M solution of MeLi in Et$_2$O (42.4 mmol) were added dropwise. At the end of the addition, the resulting brown solution was stirred for 2 more hours at room temperature, and then added dropwise (over 2.5 hours) to 2.64 mL of MeI (42 mmol) in 100 mL THF cooled to −10° C. At the end of the addition, the mixture was allowed to reach room temperature and was stirred overnight. The thus obtained yellow-brown solution was quenched with 100 mL H$_2$O; the organic layer was separated and the water layer was extracted twice with Et$_2$O; the organic layers combined, dried over MgSO$_4$ and filtered. After removing the solvents in vacuum, 5.61 g of oily product were obtained, which were analyzed by G.C./M.S. and $^1$H NMR. The product bis(3-methyl-2-indenyl)methane (purity 85% by G.C.) was obtained in 84% yield.

$^1$H NMR (CDCl$_3$): δ 7.2–7.5 (m, 8H); 3.73 (s, 2H); 3.35 (s, 4H); 2.29 (s, 6H).

(a-2) Synthesis of bis(3-methyl-2-indenyl)methane from 3-methyl-indene

In a 500 mL flask equipped with magnetic stirring bar were introduced 14.8 g (0.114 moles) of 3-methyl-indene, 2.3 g (0.077 moles) of para-formaldehyde and 4.37 g (0.023 moles) of para-toluenesulphonic acid in 200 ml of toluene; the mixture was heated to 80° C. and was maintained under stirring for 1 hour at 80° C. Then the reaction was quenched with water/NaHCO$_3$; the conversion, measured by gas chromatographic analysis, was 85.9%. The organic layer was separated, washed with water and brought to dryness under reduced pressure. The crude product was crystallized upon standing at room temperature, and then was further purified by washing with pentane or MeOH, thus isolating 15.5 g of bis(3-methyl-2-indenyl)methane (purity of 89.8% by G.C.; yield=89.8%).

The results of the $^1$H-NMR analysis correspond to the ones reported above.

(b) Synthesis of methylene-bis(1-methyl-2-indenyl)zirconium dichloride 6.5 g of bis(3-methyl-2-indenyl)methane (purity 90% by G.C., 21.5 mmol), obtained as reported above, were dissolved in 160 mL Et$_2$O, in a Schlenk tube with magnetic stirring bar; the solution was cooled to −20° C. and 27 mL of a 1.6 M solution of BuLi in hexane (43.2 mmol) were added dropwise in 15 minutes. The obtained solution was allowed to warm to room temperature and stirred for 5 hours, obtaining a red suspension, which was then cooled to −80° C. and added to a slurry of 5 g of ZrCl$_4$ (MW=233.03, 21.4 mmol) in 160 mL of pentane, in a 500 mL flask, at −80° C. After warming to room temperature, the mixture was stirred overnight. The yellow suspension was dried to a free-flowing powder; said powder was then washed with pentane ($^1$H-NMR analysis showed the presence of both rac- and meso-CH$_2$(1-Me-2-Ind)$_2$ZrCl$_2$), transferred into an extraction apparatus and finally extracted with refluxing CH$_2$Cl$_2$; a yellow precipitate formed in the collecting flask during the extraction. At the end of the extraction, CH$_2$Cl$_2$ was concentrated to 20 mL and filtered. The residue was washed with Et$_2$O and pentane, and finally dried, to yield 2.98 g of yellow solid. $^1$H NMR analysis showed the presence of the pure target product rac-CH$_2$(1-Me-2-Ind)$_2$ZrCl$_2$.

$^1$H NMR (CD$_2$Cl$_2$, ref. CDHCl$_2$ at 5.383 ppm, room temp.): Cp-CH$_3$, 2.535, s; CH$_2$, 4.375, s; Cp-H, 5.974, s; Ar, 7.2–7.4, m; 7.5–7.6, m.

Synthesis 4

Rac-Methylene-bis(1-methyl-2-indenyl)zirconium dimethyl 0.37 g of rac-CH$_2$(1-Me-2-Ind)$_2$ZrCl$_2$, obtained as reported in Synthesis 3, were slurried into 20 mL THF and cooled to 0° C.; 0.7 mL of a 1.6 M solution of MeLi in Et$_2$O (1.12 mmol), diluted in 5 mL Et$_2$O, were added. The appearance changed from a yellow suspension to a brick-red solution. After 2 hours at room temperature, the mixture was brought to dryness in vacuum, to give a dark red solid, which was extracted with 100 mL pentane at 30° C. The obtained extract was concentrated to 10 mL and cooled to −20° C., thus obtaining a precipitate. After filtration, the residue was washed with pentane and dried in vacuum to give 0.2 g of the target product rac-CH$_2$(1-Me-2-Ind)$_2$ZrMe$_2$.

$^1$H NMR (C$_6$D$_6$, room temp., ref. C$_6$D$_5$H at 7.289 ppm): Zr—CH$_3$, −0.587, s; Cp-CH$_3$, 2.137, s; CH$_2$, 3.404, s; Cp-H, 5.526, s; Ar, 7.07–7.14, m; 7.49–7.57, m.

Synthesis 5

Rac-Methylene-bis(1-methyl-2-indenyl)zirconium monomethyl monochloride

The procedure reported in synthesis 3(b) was followed, with the difference that 3 equivalents of MeLi per equivalent of bis(3-methyl-2-indenyl)methane were used, i.e. were used 27 mL of a 1.6 M solution of BuLi in hexane (64.5 mmol), thus obtaining the target product.

$^1$H NMR (CD$_2$Cl$_2$, ref. CDHCl$_2$ at 5.38 ppm, room temp.): Zr—CH$_3$, −0.50, s; Cp-CH$_3$, 2.57, s, 2.38, s; CH$_2$, 3.99, s; Cp-H, 5.55, s, 6.12, s; Ar, 7.1–7.4, m, 7.4–7.7, m.

Synthesis 6

Rac-Methylene-bis(1-phenyl-2-indenyl)zirconium dichloride (a) Synthesis of bis(3-phenyl-2-indenyl)methane In a 500 mL flask equipped with magnetic stirring bar were introduced 4.46 g (0.023 moles) of 1-phenyl-indene, 0.35 g (0.0117 moles) of formalin and 0.88 g (0.0046 moles) of para-toluenesulphonic acid in 200 ml of toluene; the mixture was heated to 80° C. and was maintained under stirring for 6 hours at 80° C. Then the reaction was quenched with water/NaHCO$_3$; the organic layer was separated, washed with water and brought to dryness under reduced pressure. The crude product was crystallized upon standing at room temperature, and then was further purified by washing with pentane or MeOH, thus isolating 4.5 g of bis(3-phenyl-2-indenyl)methane (purity of 97.3% by G.C.; yield=95.2%).

$^1$H NMR (CDCl$_3$): δ 7.1–7.7 (m, 18H); 3.76 (s, 2H); 3.39 (s, 4H).

(b) Synthesis of methylene-bis(1-phenyl-2-indenyl)zirconium dichloride 3.5 g of bis(3-phenyl-2-indenyl)methane (purity 97.3% by G.C., 8.59 mmol), obtained as reported above, were slurried in 70 mL Et$_2$O, in a Schlenk tube with magnetic stirring bar; the solution was cooled to −80° C. and 7.5 mL of a 2.5 M solution of BuLi in hexane (18.75 mmol) were added dropwise in 15 minutes. The obtained solution was allowed to warm to room temperature and stirred for 6 hours, thus obtaining a light brown suspension, which was then cooled to −80° C. and added to a slurry of 2 g of ZrCl$_4$ (8.58 mmol) in 80 mL of pentane, in a 250 mL flask, at −80° C. After warming to room temperature the mixture was stirred overnight. The yellow suspension was concentrated to 30 mL, filtered, dried and then extracted with refluxing CH$_2$Cl$_2$ until the extract was colorless (a yellow precipitate formed in the collecting flask during the extraction). At the end of the extraction, CH$_2$Cl$_2$ was concentrated to 15 mL, then cooled to −20° C. overnight, and finally filtered. The residue was washed with CH$_2$Cl$_2$ until the washing turned from brown to yellow, and finally dried, to yield 2.2 g of yellow solid. $^1$H NMR analysis showed the presence of pure target product CH$_2$(1-Ph-2-Ind)$_2$ZrCl$_2$.

$^1$H NMR (CD$_2$Cl$_2$, ref. CDHCl$_2$ at 5.377 ppm, room temp.): CH$_2$, 4.770, s; Cp-H, 5.633, s; Ar, 7.2–8, m.

Additional 0.25 g of the target product were recovered from the filtrate and washings, combined and concentrated to 8 mL, cooled to −20° C. overnight, filtered and dried. The combined yield was 51.3%.

Synthesis 7

Rac-Methylene-bis(1-t-butyl-2-indenyl)zirconium dichloride (a-1) Synthesis of bis(3-t-butyl-2-indenyl)methane (with para-formaldehyde and para-toluenesulphonic acid, in toluene)

In a 500 mL flask equipped with magnetic stirring bar were introduced 12.35 g (0.072 moles) of 1-t-butyl-indene, 1.43 g (0.048 moles) of para-formaldehyde and 2.73 g (0.014 moles) of para-toluenesulphonic acid in 200 ml of toluene; the mixture was heated to 80° C. and was maintained under stirring for 6 hours at 80° C. Then the reaction was quenched with water/NaHCO$_3$; the conversion, measured by gas chromatographic analysis, was 79.5%. The organic layer was separated, washed with water and brought to dryness under reduced pressure. The crude product crystallized upon standing at room temperature, and then was further purified by washing with MeOH, thus isolating 10.8 g bis(3-t-butyl-2-indenyl)methane (purity of 90.9 by G.C.; yield=76.81%).

$^1$H NMR (CDCl$_3$): δ 7.6–7.8 (d, 2H); 7.1–7.4 (m, 6H); 4.23 (s, 2H); 3.34 (s, 4H); 1.58 (s, 18H).

(a-2) Synthesis of bis(3-t-butyl-2-indenyl)methane (with dioxolane and para-toluenesulphonic acid, in toluene)

4.1 g of para-toluenesulphonic acid (21.6 mmol), 200 mL of toluene, 7.6 mL of 1,3-dioxolane (Aldrich, MW 74.08, 108.8 mmol) and 19.0 g of 3-t-Bu-indene (MW 172.16, 110 mmol) were placed in this order in a 0.5 L flask equipped with magnetic stirring bar, thermometer and reflux condenser. This mixture was heated at 80° C. in 20 minutes and stirred at 80° C. for 6 hours. After cooling to room temperature, the mixture was poured onto ice/NaHCO$_3$ and the organic layer separated in a funnel. The water layer was washed with Et$_2$O (2×150 mL), the organic layers were combined, dried with NaSO$_4$, filtered and concentrated in vacuo to yield a red paste (18.6 g) which has a content of 82% of the target product (77% conversion). This paste was taken up in 50 mL of pentane, stirred 30 min and filtered. The residue was dried in vacuo: yield 7.0 g of an ochre powder (purity 97.5% by G.C., yield 34.8% of pure product).

$^1$H-NMR (CDCl$_3$, δ, ppm): 1.57, s, 18H, t-Bu; 3.32, s, 4H, CH$_2$ indene; 4.21, s, 2H, CH$_2$ bridge, 7–7.5, m, 6H, Ar; 7.67, 7.71, d, 2H, Ar.

(a-3) Synthesis of bis(3-t-butyl-2-indenyl)methane (with dioxolane and para-toluenesulphonic acid, in n-decane)

The procedure reported above in Synthesis 7(a-2) was repeated, using 2.07 g of para-toluenesulphonic acid (11 mmol), 100 mL of n-decane, 3.8 mL of 1,3-dioxolane (Aldrich, MW 74.08, 55 mmol) and 9.4 g of 3-t-Bu-indene (MW 172.16, 55 mmol); the reaction mixture was heated at 100° C. in 20 minutes and stirred at 100° C. for 6 hours. The target product was obtained with 82% conversion.

(a-4) Synthesis of bis(3-t-butyl-2-indenyl)methane (with dioxolane and H$_2$SO$_4$, in toluene)

The procedure reported above in Synthesis 7(a-2) was repeated, using 1.05 g of H$_2$SO$_4$ (10 mmol), 100 mL of toluene, 3.74 mL of 1,3-dioxolane (Aldrich, MW 74.08, 54 mmol) and 9.23 g of 3-t-Bu-indene (MW 172.16, 54 mmol); the reaction mixture was heated at 80° C. in 20 minutes and stirred at 80° C. for 6 hours. The target product was obtained with 29.2% conversion.

(b) Synthesis of methylene-bis(1-t-butyl-2-indenyl) zirconium dichloride 3 g of bis(3-t-butyl-2-indenyl)methane (purity 93.1% by G.C., 7.83 mmol), obtained as reported above, were dissolved in 63 mL Et$_2$O, in a Schlenk tube with magnetic stirring bar; the solution was cooled to −80° C. and 10.6 mL of a 1.6 M solution of BuLi in hexane (16.96 mmol) were added dropwise in 15 minutes. The obtained solution was allowed to warm to room temperature and stirred for 5 hours, thus obtaining a red suspension, which was then cooled to −80° C. and added to a slurry of 1.96 g of ZrCl$_4$ (8.41 mmol), in 63 mL of pentane, in a 250 mL flask, at −80° C. After warming to room temperature, the mixture was stirred overnight. The yellow suspension was dried to a free-flowing powder. $^1$H NMR analysis showed the presence of the target product rac-CH$_2$(1-t-Bu-2-Ind)$_2$ZrCl$_2$ as the only isomer. The powder was slurried in 100 mL of CH$_2$Cl$_2$, transferred into an extraction apparatus and extracted with refluxing CH$_2$Cl$_2$ for 6 hours (a yellow precipitate formed in the collecting flask during the extraction). At the end of the extraction, CH$_2$Cl$_2$ was concentrated to 10 mL and then filtered. The residue was washed with pentane, until the washing was colorless, and was dried to yield 1.757 g of a yellow solid. $^1$H NMR analysis showed the presence of the pure target product rac-CH$_2$(1-t-Bu-2-Ind)$_2$ZrCl$_2$.

$^1$H NMR (CD$_2$Cl$_2$, ref. CDHCl$_2$ at 5.377 ppm, room temp.): t-Bu, 1.719, s; CH$_2$, 4.926, s; Cp-H, 6.220, s; Ar, 7.2–7.3, m; 7.4–7.5, m, 7.8–7.9, m.

Additional 0.4 g of product were recovered from the filtrate, by recrystallization from toluene and washing with Et$_2$O. The combined yield was 55%.

Synthesis 8

Rac-Methylene-bis(1-t-butyl-2-indenyl)hafnium dimethyl 1.8 g of bis(3-t-butyl-2-indenyl)methane (purity 97.7% by G.C., 4.9 mmol), obtained as reported in Synthesis 7(a), were dissolved in 30 mL Et$_2$O, in a 250 mL Schlenk tube with magnetic stirring bar, and 12.6 mL of a 1.6 M solution of MeLi in Et$_2$O (20.16 mmol) were added dropwise in 5 minutes, at room temperature (exothermic reaction); after 10 minutes, a white suspension was obtained. The mixture was maintained under stirring for 2 hours and the suspension was then cooled to −80° C.; a slurry of 1.62 g of HfCl$_4$ (Roc-Ric, 99.99%, MW=320.3, 50.6 mmol) in 30 mL of pentane, also cooled to −80 ° C., was added. The mixture was stirred overnight by letting the temperature rise slowly to room temperature in the Dewar. The gray suspension was concentrated in vacuo to remove the solvents to give a free-flowing powder, which was extracted in a Soxhlet for 4.5 hours with 100 mL of pentane. The extract was dried to a yellow powder (1.46 g).

$^1$H NMR analysis showed the presence of a mixture of products. These products were taken up in 10 mL of pentane, stirred and filtered; the obtained residue (0.3 g), in the form of a light yellow powder, was rac-CH$_2$(1-t-Bu-2-Ind)$_2$HfMe$_2$ containing a small amount of impurities. The pentane soluble fraction was concentrated, treated with 2 mL of Et$_2$O and cooled to −20° C.

After three days, 50 mg of chemically pure (by $^1$H NMR) rac-CH$_2$(1-t-Bu-2-Ind)$_2$HfMe$_2$ were recovered by filtration.

Synthesis 9

Rac-Methylene-bis(1-trimethylsilyl-2-indenyl)zirconium dichloride (a) Synthesis of bis(3-trimethylsilyl-2-indenyl)methane 6.0 g of bis(2-indenyl)methane (M$_W$=244.33, 77%, 18.9 mmol), obtained as described in Synthesis 1(a), were dissolved in 70 mL Et$_2$O, cooled to −50° C. and treated with 16 mL of BuLi 2.5 M in hexane (39.8 mmol). The thus obtained orange suspension was allowed to reach room temperature, stirred for 5 hours, then added to a solution of 5 mL of Me$_3$SiCl (d=0.856, 4.3 g, MW 108.64, 39.8 mmol) in 30 mL of Et$_2$O previously cooled at −30° C. The yellow suspension was allowed to reach room temperature and stirred overnight, then quenched with MeOH and filtered; the filtrate was finally brought to dryness to yield 8.2 g of bis(1-trimethylsilyl-2-indenyl)methane, in form of a clear, thick orange oil (M$_W$ 388.07, purity 71.5% by G.C.).

(b) Synthesis of methylene-bis(1-trimethylsilyl-2-indenyl) zirconium dichloride 8.0 g of bis(1-trimethylsilyl-2-indenyl)methane (purity 71.5% by G.C., 14.6 mmol) were dissolved in 70 mL Et$_2$O in a Schlenk tube with magnetic stirring bar; the orange solution was cooled to −50° C. and 17.3 mL of a 2.5 M solution of BuLi in hexane (43.2 mmol) were added dropwise in 5 minutes (red solution); the obtained solution was allowed to warm to room temperature and stirred for 5 hours, obtaining a brick-red suspension, which was then cooled to −30° C. and added to a slurry of 4.8 g of ZrCl$_4$ (M$_W$=233.03, 20.6 mmol) in 50 mL of toluene, in a 250 mL flask at −30° C. After warming to room temperature, the yellow mixture was stirred overnight. The yellow suspension was concentrated in vacuo to remove Et$_2$O and then filtered. The contents of the toluene solution were discarded following $^1$H-NMR analysis. The yellow residue on the filter (9.12 g of the target product, containing LiCl) was extracted with refluxing CH$_2$Cl$_2$ (Soxhlet, 7 hours).

The residue (6.0 g) was pure rac-methylene(1-trimethylsilyl-2-indenyl)$_2$ZrCl$_2$ containing LiCl, while the extract (2.75 g) contained some impurities and some meso isomer.

Synthesis 10

Rac-Methylene-bis(1-trimethylsilyl-3-methyl-2-indenyl) zirconium dichloride (a) Synthesis of bis(1-trimethylsilyl-3-methyl-2-indenyl)methane 8.05 mmol of bis(3-methyl-2-indenyl)methane, obtained as described above in Synthesis 3(a-1), were dissolved in 50 mL Et$_2$O, cooled to −50° C. and treated with 6.7 mL of BuLi 2.5 M in hexane (17 mmol). The thus obtained red-violet suspension was allowed to reach room temperature, then added to a solution of 2.2 mL of Me$_3$SiCl in 30 mL of Et$_2$O previously cooled at −30° C. The suspension was allowed to reach room temperature (the color fades) and stirred overnight, then quenched with MeOH (the color turns yellow) and filtered; the filtrate was brought to dryness to yield bis(1-trimethylsilyl-3-methyl-2-indenyl)methane in the form of a brown-orange liquid (3.55 g, 100% yield).

(b) Synthesis of methylene-bis(1-trimethylsilyl-3-methyl-2-indenyl)zirconium dichloride 3.55 g of bis(1-trimethylsilyl-3-methyl-2-indenyl)methane (8.53 mmol) were dissolved in 50 mL Et$_2$O in a Schlenk tube with magnetic stirring bar; the obtained orange solution was cooled to −50° C. and 7.2 mL of a 2.5 M solution of BuLi in hexane (18 mmol) were added dropwise in 5 minutes (red solution); the resulting solution was allowed to warm to room temperature and stirred overnight, obtaining a darker red solution, which was then cooled to −30° C. and added to a slurry of 1.98 g of ZrCl$_4$ (M$_W$=233.03, 8.53 mmol) in 50 mL of toluene, in a 250 mL flask at −30° C. After warming to room temperature, the brown-violet mixture was stirred overnight. The brown suspension was concentrated in vacuo to remove Et$_2$O and then filtered. The residue was discarded following $^1$H-NMR analysis; the toluene solution was brought to dryness, then washed with 50 mL Et$_2$O, filtered, the residue discarded and the filtrate dried again to 3.2 g of a brown product which was then washed with pentane; the residue dried in vacuo (1.75 g). $^1$H-NMR analysis showed the presence of pure rac-CH$_2$(1-Me-3-TMS-2-Ind)$_2$ZrCl$_2$ as the only isomer.

Synthesis 11
Rac-Methylene-bis(1-diphenylphosphino-2-indenyl)zirconium dichloride (a) Synthesis of bis(3-diphenylphosphino-2-indenyl)methane 8.17 g of bis(2-indenyl)methane (M$_W$=244.33, 77%, 18.9 mmol), obtained as described in Synthesis 1(a), were dissolved in 100 mL Et$_2$O, cooled to −50° C. and treated with 21.6 mL of BuLi 2.5 M in hexane (54.1 mmol). The thus obtained yellow suspension was allowed to reach room temperature, stirred for 5 hours, then added to a solution of 9.7 mL of Ph$_2$PCl (MW 220.64, 54.13 mmol) in 30 mL of Et$_2$O previously cooled at −50° C. The yellow suspension was allowed to reach room temperature (the color fades) and stirred overnight; it was then quenched with MeOH and filtered, and the filtrate brought to dryness to yield 13.5 g of an ochre powder, which was washed with pentane (washing discarded) and then with Et$_2$O (washing discarded); the residue was dried to give 8.3 g of pure bis(3-diphenylphosphino-2-indenyl)methane.

The residue from the filtration of the crude reaction mixture (6.7 g) were extracted with refluxing CH$_2$Cl$_2$ to give the same product.

(b) Synthesis rac-methylene-bis(1-diphenylphosphino-2-indenyl)zirconium dichloride 6.9 g bis(3-diphenylphosphino-2-indenyl)methane (M$_W$=612, 11.3 mmol) were suspended in 100 mL Et$_2$O in a Schlenk tube with magnetic stirring bar, cooled to −50° C. and 9.5 mL of a 2.5 M solution of BuLi in hexane (23.7 mmol) were added dropwise in 5 minutes; the solution was allowed to warm to room temperature and stirred for 5 hours, thus obtaining an ochre suspension, which was then cooled to −30° C. and added to a slurry of 2.6 g of ZrCl$_4$ (M$_W$=233.03, 11.3 mmol) in 20 mL of toluene, in a 250 mL flask at −30° C. After warming to room temperature, the mixture was stirred overnight. The yellow suspension was filtered. The solution was discarded; the yellow residue was dried to a free-flowing powder (8.9 g), and then extracted with refluxing CH$_2$Cl$_2$ to give 6.5 g of yellow powder. $^1$H-NMR analysis showed the presence of pure rac-CH$_2$(1-Ph$_2$P-2-Ind)$_2$ZrCl$_2$ as the only isomer.

Polymerization Tests

EXAMPLES 1–4 AND 4'

Comparative Example 1
Propylene Homopolymerization

Propylene was charged at room temperature in a 1-L or 4.25-L jacketed stainless-steel autoclave, equipped with magnetically driven stirrer and a 35-ml stainless-steel vial, connected to a thermostat for temperature control, previously purified by washing with a AliBu$_3$ solution in hexane and dried at 50° C. in a stream of propylene. AliBu$_3$ (1 mmol in hexane) was added as scavenger before the monomer.

The autoclave was then thermostatted at 2° C. below the polymerization temperature and then a toluene solution containing a mixture of catalyst and cocatalyst, in the amounts reported in Table 1, was injected into the autoclave, by means of nitrogen pressure through the stainless-steel vial. The temperature was rapidly raised to the polymerization temperature and the polymerization was performed at constant temperature for 1 hour.

After having vented the unreacted monomer and having cooled the reactor to room temperature, the polymer was dried under reduced pressure, at 60° C.

The polymerization conditions and the characterization data of the obtained polymers are reported in Table 1.

From the obtained results, it is evident that the catalysts containing the methylene-bridged metallocenes of the present invention are unexpectedly much more active than the unsubstituted analogue methylene-bis(2-indenyl)zirconium dichloride. More specifically, the prior art metallocene of Comparative Example 1 proved to be totally inactive in propylene polymerization.

Moreover, the results of Table 1 demonstrate that, by using hafnium metallocenes, it is possible to obtain polymers having higher intrinsic viscosity with respect to polymers obtained with the corresponding zirconocenes.

EXAMPLES 5–7

Ethylene Homopolymerization

A 1 L stainless-steel autoclave, equipped with magnetic stirrer, temperature indicator and feeding line for the ethylene, was thermostatted with H$_2$O/steam and purified by purging with ethylene at 80° C. Under ethylene purge, 400 mL of n-hexane and 2 mmol TIBA were added; the temperature was brought to 80° C. and the reactor was vented to remove residual nitrogen. The reactor was then pressurized with ethylene up to 11 bar-a. The catalyst solution, comprising the amount of catalyst and cocatalyst reported in Table 3, was injected into the autoclave with ethylene overpressure and the ethylene partial pressure was stabilized to 9.6 bar-a (Ptot=11 bar-a). Polymerization was carried out at 80° C. for the time specified in Table 2, by maintaining a constant ethylene partial pressure. The polymerization was interrupted by degassing unreacted ethylene; the thus obtained polymer was isolated by filtration and dried in vacuum at 60° C.

The polymerization conditions and results are reported in Table 2; the characterization data of the obtained polymers are indicated in Table 3.

From the results reported in Table 3, it is evident that the methylene-bridged metallocenes according to the present invention are able to yield linear α-olefins, having low values of Pn (Number Average Degree of Polymerization)

and having a number of terminal vinyl unsaturations up to 100% of the total number of terminal unsaturations. Therefore, by varying the substitution pattern on the catalysts according to the invention, it is possible to obtain linear α-olefins having a percentage of terminal vinyl unsaturations higher than 90%, thus providing PE waxes having low Pn.

The polymer obtained in Example 5 was further characterized by $^{13}$C-NMR analysis; it resulted that said polymer is a linear α-olefin containing 0.29% of $C_2$ branches and 0.16% of $C_{\geq 6}$ branches.

EXAMPLES 8–11

Comparative Examples 2–4

Ethylene Homopolymerization

A 200 mL glass autoclave, provided with magnetic stirrer, temperature indicator and feeding line for ethylene, was purified and fluxed with ethylene at 35° C. At room temperature were introduced 90 ml of hexane.

The catalytic system was prepared separately in 10 ml of heptane by consecutively introducing the cocatalyst reported in Table 2 and, after 5 minutes under stirring, the metallocene reported in Table 2, solved in the lowest possible amount of toluene.

After 5 minutes under stirring, the solution was introduced into the autoclave under ethylene flow; the reactor was closed and the temperature risen to 80° C. The autoclave was then pressurized to 4.6 barg and the total pressure was kept constant by feeding ethylene.

After the polymerization time reported in Table 2, the reaction was stopped by cooling and degassing the reactor, and by introducing 1 ml MeOH. The obtained polymer was washed with acidic MeOH, the with MeOH and finally dried under vacuum in oven at 60° C.

The polymerization conditions and results are reported in Table 2; the characterization data of the obtained polymers are indicated in Table 3.

From the results reported in Table 2, it is evident that the methylene-bridged metallocenes according to the present invention are unexpectedly much more active than the unsubstituted analogue methylene-bis(2-indenyl)zirconium dichloride.

Moreover, the results of Table 3 clearly show that, by changing the substitution pattern of the methylene-bridged metallocenes of the invention, it is possible to obtain in high yields polyethylenes having intrinsic viscosity (I.V.) ranging from very low values (oils) to high values, thus allowing polymers having a wide range of molecular weights to be obtained.

EXAMPLE 12

Ethylene/1-hexene Copolymerization

A 200 mL glass autoclave, provided with magnetic stirrer, temperature indicator and feeding line for ethylene, was purified and fluxed with ethylene at 35° C. At room temperature were introduced 85 ml of heptane and 5 ml of 1-hexene.

The catalytic system was prepared separately in 10 ml of heptane by consecutively introducing 0.26 mmol of MAO and, after 5 minutes under stirring, 0.1 mg rac-methylene-bis(1-methyl-2-indenyl)zirconium dimethyl (Al/Zr ratio= 1000) solved in the lowest possible amount of toluene.

After 5 minutes under stirring, the solution was introduced into the autoclave under ethylene flow; the reactor was closed and the temperature risen to 70° C. The autoclave was then pressurized to 4.5 barg and the total pressure was kept constant by feeding ethylene. After 10 minutes, the polymerization was stopped by cooling and degassing the reactor, and by introducing 1 ml MeOH. The obtained polymer was washed with acidic MeOH, the with MeOH and finally dried under vacuum in oven at 60° C., thus obtaining 2.7 g (Activity=695.7 kg/gCat.h) of a ethylene/1-hexene copolymer in the form of an oil, having I.V. of 0.12 dl/g and having a total number of branches equal to 4.5 branches/100 carbon atoms (determined by $^{13}$C-NMR); more specifically, no methyl branches were detected, while about 90% of the total branches was attributable to butyl or higher branches.

EXAMPLE 13

Ethylene/propylene Copolymerization

A 2.3 L steel autoclave, provided with magnetic stirrer, temperature and pressure controls and indicators and feeding line for the monomers, was purified and fluxed with ethylene at 80° C.

At room temperature were introduced 1000 ml of hexane and 6.0 g of propylene, the temperature risen to 70° C. and the autoclave was pressurized with 9.5 bar of ethylene. The catalytic system was prepared separately in 10 ml Schlenk tube by consecutively introducing 2.31 mmol of MAO (1) and 0.5 mg of rac-methylene-bis(1-methyl-2-indenyl) zirconium dichloride (Al/Zr=2000 as molar ratio) solved in the lowest possible amount of toluene.

After 10 minutes under stirring at 25° C., the solution was injected into the autoclave trough a vial by an ethylene overpressure. The total pressure (10 barg) was kept constant by feeding a mixture of ethylene/propylene in a molar ratio of 37.

After 90 minutes, the polymerization was stopped by cooling and introducing 1 bar of carbon monoxide. Then the reactor was degassed and the recovered milky solution was separated from the solvent. 142 g (1350 Kg/gZr) of polymer were obtained, after drying in oven at 60° C. under vacuum. The polymer was analyzed and showed I.V.=0.20 dl/g, Tm=97.1° C. and $_A$H=158 J/g.

The total branching content, analyzed by NMR analysis, was 2.65/100 carbon atoms.

EXAMPLES 14–19

Ethylene Homopolymerization

The following polymerization procedure, similar to the one described in examples 5–7 was followed: a 1 L stainless-steel autoclave, equipped with magnetic stirrer, temperature indicator and feeding line for the ethylene, was thermostatted with $H_2O$/steam and purified by purging with ethylene at 80° C. Under ethylene purge, 500 mL of n-hexane and 1 mmol TIBA were added; the temperature was brought to 80° C. and the reactor was vented to remove residual nitrogen. The reactor was then pressurized with ethylene up to 11 bar-a. The catalyst solution, comprising the amount of catalyst and cocatalyst reported in Table 3, was injected into the autoclave with ethylene overpressure and the ethylene partial pressure was stabilized to 9.6 bar-a (Ptot=11 bar-a). Polymerization was carried out at 80° C. for the time specified in Table 2, by maintaining a constant ethylene partial pressure. The polymerization was interrupted by degassing unreacted ethylene; the thus obtained polymer was isolated by filtration and dried in vacuum at 60° C.

The polymerization conditions and results are reported in Table 2; the characterization data of the obtained polymers are indicated in Table 3.

TABLE 1

Propylene homopolymerization

| Ex. | Metallocene Type | MAO (µmol) | | (mmol) | Al/Zr (mol) | T (° C.) | Yield (g) | Activity (Kg/gCat.h) | Pn (dl/g) | I.V. (dl/g) |
|---|---|---|---|---|---|---|---|---|---|---|
| 1 | $CH_2(4,7\text{-}Me_2\text{-}2\text{-}Ind)_2ZrCl_2$ | 0.33 | (2) | 1.63 | 5000 | 30 | 284.87 | 1899 | Oil | 0.3 |
| 2 | $r\text{-}CH_2(1\text{-}Me\text{-}2\text{-}Ind)_2ZrMe_2$ | 12.77 | (1) | 12.76 | 1000 | 50 | 23.00 | 4.6 | 26 | n.d. |
| 3 | $r\text{-}CH_2(1\text{-}Ph\text{-}2\text{-}Ind)_2ZrCl_2$ | 1.80 | (2) | 5.39 | 3000 | 50 | 72.58 | 72.6 | 263 | 0.26 |
| 4 | $r\text{-}CH_2(1\text{-}tBut\text{-}2\text{-}Ind)_2ZrCl_2$ | 0.39 | (2) | 1.93 | 5000 | 50 | 28.25 | 141.2 | 430 | n.d. |
| 4' | $r\text{-}CH_2(1\text{-}tBut\text{-}2\text{-}Ind)_2HfMe_2$ | 3.56 | (2) | 3.55 | 1000 | 50 | 50.6 | 25.3 | n.d. | 0.83 |
| COMP. 1 | $CH_2(2\text{-}Ind)_2ZrCl_2$ | 4.94 | (2) | 7.41 | 1500 | 50 | 0 | INACTIVE | — | — |

(1) Commercial 10% w/w toluene solution of MAO (1.7 M; Witco).
(2) The commercial sample (1) was dried in vacuum to a free-flowing powder (residual $AlMe_3$ about 3–5 mol %).

TABLE 2

Ethylene homopolymerization

| Example | Metallocene Type | (mg) | Cocatalyst Type | (mmol) | Al/Zr (mol) | Time (min) | Yield (g) | Activity (Kg/gCat.h) |
|---|---|---|---|---|---|---|---|---|
| 5 | $r\text{-}CH_2(1\text{-}Me\text{-}2\text{-}Ind)_2ZrCl_2$ | 0.2 | MAO (2) | 2.31 | 5000 | 23 | 83 | 1092 |
| 6 | $r\text{-}CH_2(1\text{-}t\text{-}Bu\text{-}2\text{-}Ind)_2ZrCl_2$ | 0.2 | MAO (2) | 1.93 | 5000 | 20 | 18 | 272.7 |
| 7 | $r\text{-}CH_2(1\text{-}Ph\text{-}2\text{-}Ind)_2ZrCl_2$ | 0.2 | MAO (1) | 0.18 | 500 | 60 | 12.4 | 62.0 |
| 8 | $r\text{-}CH_2(1\text{-}Me\text{-}2\text{-}Ind)_2ZrMe_2$ | 0.1 | TIOAO | 0.27 | 1000 | 15 | 0.76 | 130.6 |
| 9 | $r\text{-}CH_2(1\text{-}Me\text{-}2\text{-}Ind)_2ZrMeCl$ | 0.1 | MAO (2) | 0.24 | 1000 | 10 | 6.2 | 1681 |
| 10 | $r\text{-}CH_2(1\text{-}Me\text{-}2\text{-}Ind)_2ZrMeCl$ | 0.3 | TIOAO | 1.4 | 2000 | 10 | 2.6 | 235 |
| 11 | $r\text{-}CH_2(1\text{-}t\text{-}Bu\text{-}2\text{-}Ind)_2ZrCl_2$ | 0.1 | MAO (2) | 0.97 | 5000 | 10 | 1.34 | 455.5 |
| 14 | $r\text{-}CH_2(1\text{-}TMS\text{-}2\text{-}Ind)_2ZrCl_2$ | 0.5 | MAO (1) | 0.45 | 500 | 60 | 41.7 | 83.4 |
| 15 | $r\text{-}CH_2(1\text{-}Me\text{-}3\text{-}TMS\text{-}2\text{-}Ind)_2ZrCl_2$ | 1.0 | MAO (1) | 1.74 | 1000 | 60 | 29.0 | 29.0 |
| 16 | $r\text{-}CH_2(1\text{-}Me\text{-}3\text{-}TMS\text{-}2\text{-}Ind)_2ZrCl_2$ | 0.2 | MAO (1) | 0.17 | 500 | 60 | 15.5 | 77.5 |
| 17 | $r\text{-}CH_2(1\text{-}Bz\text{-}2\text{-}Ind)_2ZrCl_2$ | 0.5 | MAO (1) | 0.43 | 500 | 60 | 12.6 | 25.2 |
| 18 | $r\text{-}CH_2(1\text{-}Ph\text{-}2\text{-}Ind)_2ZrCl_2$ | 0.2 | MAO (1) | 0.45 | 500 | 60 | 21.3 | 42.6 |
| 19 | $r\text{-}CH_2(4,7\text{-}Me_2\text{-}2\text{-}Ind)_2ZrCl_2$ | 0.5 | MAO (1) | 0.54 | 500 | 60 | 27.7 | 55.4 |
| COMP. 2 | $CH_2(2\text{-}Ind)_2ZrCl_2$ | 0.3 | MAO (2) | 0.75 | 1000 | 10 | 1.51 | 30.2 |
| COMP. 3 | $CH_2(2\text{-}Ind)_2ZrCl_2$ | 0.5 | MAO (2) | 0.5 | 2000 | 10 | 3.39 | 40.8 |
| COMP. 4 | $CH_2(2\text{-}Ind)_2ZrCl_2$ | 0.5 | TIOAO | 2.50 | 2000 | 30 | 1.54 | 27.1 |

(1) Commercial 10% w/w toluene solution of MAO (1.7 M; Witco).
(2) The commercial sample (1) was dried in vacuum to a free-flowing powder (residual $AlMe_3$ about 3–5 mol %).

TABLE 3

Ethylene homopolymerization

| Example | I.V. (dl/g) | Pn | ΔH (J/g) | $T_m$ (° C.) | Terminal vinyl unsaturations (%) | Terminal vinylidene unsaturations (%) |
|---|---|---|---|---|---|---|
| 5 | 0.21 | 108 | 197 | 120 | 94.1 | 8.5 |
| 6 | 1.83 | 2141 | 203 | 135 | n.d. | n.d. |
| 7 | 2.24 | 2829 | 170 | 142 | n.d. | n.d. |
| 8 | 0.29 | n.d. | n.d. | n.d. | n.d. | n.d. |
| 9 | 0.21 | n.d. | 185 | 119 | n.d. | n.d. |
| 10 | 0.22 | n.d. | n.d. | n.d. | n.d. | n.d. |
| 11 | 1.65 | n.d. | n.d. | n.d. | n.d. | n.d. |
| 14 | 0.9 | 804 | 218 | 132 | 100 | 0 |
| 15 | 0.85 | 743 | n.d. | n.d. | 86.8 | 13.2 |
| 16 | n.d. | n.d. | n.d. | n.d. | 100 | 0 |
| 17 | 0.33 | 202 | 212 | 123 | 95.9 | 4.1 |
| 18 | 1.87 | 2206 | 192 | 139 | n.d. | n.d. |
| 19 | 0.89 | 792 | 186 | 129 | 72.5 | 27.5 |
| COMP. 2 | 0.17 | 81 | 217 | 125 | 91.5 | 8.5 |
| COMP. 3 | 0.12 | 50 | n.d. | n.d. | n.d. | n.d. |
| COMP. 4 | 0.2 | n.d. | n.d. | n.d. | n.d. | n.d. |

What is claimed is:
1. A ligand of formula (II):

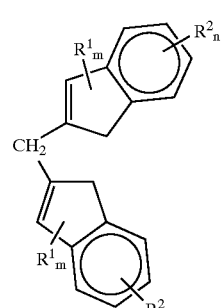

wherein the substituents $R^1$ and $R^2$, the same or different from each other, are selected from the group consisting of linear or branched, $C_1$–$C_{20}$ aliphatic hydrocarbon, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements, —OR, —SR, —$NR_2$, N-pyrrolyl, N-indolyl, —$PR_2$, —$BR_2$ and —$SiR_3$ groups; m is an integer ranging from 0 to 2; n is an integer ranging from 0 to 4; with the proviso that, when m is 0, then n is different from 0.

2. A process for the preparation of a ligand as described in claim 1, comprising reacting formaldehyde or a derivative thereof with an indene of formula (III):

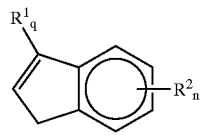

(III)

wherein $R^1$, $R^2$ and n have the meaning reported in claim 1, and q is 0 or 1, in the presence of a Brønsted acid, the molar ratio between said compound (III) and formaldehyde of a derivative thereof being $\geq 1$.

3. The process according to claim 2, characterized by being carried out in an aprotic solvent.

4. The process according to claim 3, wherein said aprotic solvent is toluene or n-decane and said acid is selected from the group consisting of p-toluensulphonic acid, acetic acid, methanesulphonic acid, HCl, $H_2SO_4$, $HBF_4$ and mixtures thereof.

5. The process according to claim 2, wherein said formaldehyde or a derivative thereof is selected from formalin, paraformaldehyde, 1,3-dioxolane and trioxane.

6. The process according to claim 2, wherein the molar ratio between said indene of formula (III) and formaldehyde or a derivative thereof is about 2.

* * * * *